United States Patent [19]

Dingerdissen et al.

[11] Patent Number: 5,693,825
[45] Date of Patent: Dec. 2, 1997

[54] PREPARATION OF AZIRIDINES

[75] Inventors: Uwe Dingerdissen, Seeheim-Jugenheim; Günter Lauth, Ratzenburg; Peter Trübenbach, Ludwigshafen; Ulrich Steuerle, Heidelberg, all of Germany

[73] Assignee: BASF Aktiengesellschaft, Ludwigshafen, Germany

[21] Appl. No.: 705,768

[22] Filed: Aug. 30, 1996

[30] Foreign Application Priority Data

Sep. 12, 1995 [DE] Germany .................. 195 33 662.3

[51] Int. Cl.$^6$ .................................................. C07D 203/08
[52] U.S. Cl. ........................ 548/954; 548/967; 548/968; 548/969
[58] Field of Search .............................. 548/954, 967, 548/968, 969

[56] References Cited

U.S. PATENT DOCUMENTS

| | | | |
|---|---|---|---|
| 4,289,656 | 9/1981 | Hayes et al. | 252/470 |
| 4,301,036 | 11/1981 | Childress et al. | 252/458 |
| 4,337,175 | 6/1982 | Ramirez | 252/455 R |
| 4,358,405 | 11/1982 | Hayes et al. | 260/239 E |
| 4,376,732 | 3/1983 | Ramirez | 260/239 E |
| 4,477,591 | 10/1984 | Ramirez | 502/340 |
| 4,826,799 | 5/1989 | Cheng et al. | 502/301 |
| 5,120,860 | 6/1992 | Olson et al. | 252/470 |

FOREIGN PATENT DOCUMENTS

| | | |
|---|---|---|
| 44118 | 1/1982 | European Pat. Off. . |
| 227461 | 7/1987 | European Pat. Off. . |
| 228898 | 7/1987 | European Pat. Off. . |
| 230776 | 8/1987 | European Pat. Off. . |
| 423526 | 4/1991 | European Pat. Off. . |
| 489166 | 6/1992 | European Pat. Off. . |
| WO88/07038 | 9/1988 | WIPO . |
| WO 89/05797 | 6/1989 | WIPO . |
| WO89/06229 | 7/1989 | WIPO . |

OTHER PUBLICATIONS

CA113: 152233t Method of producing aziridine . . . ethanolamines. Shimasaki et al., p. 761, 1990.
CA113: 191133e Preparation of aziridine compounds. Ariyoshi et al., p. 701, 1990.
CA117: 233833y Preparation of . . . alkanolamines. Tsuneki et al., p. 854, 1992.
CA118: 191529s Preparation of aziridine. Tsuneki et al., p. 933, 1993.

*Primary Examiner*—Joseph McKane
*Attorney, Agent, or Firm*—John H. Shurtleff

[57] ABSTRACT

A process for the preparation of an aziridine, especially ethyleneimine but also its derivatives in which one or both of its carbon atoms may be substituted once or twice by $C_1$–$C_8$-alkyl, $C_3$–$C_8$-cycloalkyl or aryl, and the nitrogen atom is substituted by hydrogen, $C_1$–$C_8$-alkyl, $C_3$–$C_8$-cycloalkyl, aryl benzyl, $C_1$–$C_8$-hydroxyalkyl or $C_1$–$C_8$-aminoalkyl wherein ethanolamine or its derivatives bearing the same carbon and nitrogen substituents is reacted in the gas phase for dehydration at from 200° to 600° C. and from 0.001 to 5 bar, especially 0.1 to 1 bar, over a heterogeneous catalyst shaped as presintered moldings and maintained as a steady-state or as a circulating fluidized bed catalyst. The preferred fluidizable presintered moldings are those prepared from a ceramic powder as a catalyst or catalyst carrier having a uniform pore size in the macroporous range.

15 Claims, No Drawings

PREPARATION OF AZIRIDINES

The present invention relates to a process for the preparation of aziridines by converting alkanolamines over sintered moldings in the gas phase.

The preparation of aziridines, in particular ethyleneimine, by dehydrating alkanolamines in the gas phase over molecular sieves comprising aluminum silicates, aluminum phosphates or silicon aluminum phosphates is disclosed in WO-A-89/05797.

U.S. Pat. No. 4,289,656, U.S. Pat. No. 4,301,036, U.S. Pat. No. 4,337,175, U.S. Pat. No. 4,358,405, U.S. Pat. No. 4,376,732 and U.S. Pat. No. 4,477,591 disclose catalysts based on niobium/tantalum oxide with the addition of alkaline earth metal oxide and/or iron/chromium oxides for the catalytic gas-phase dehydration of monoethanolamine to ethyleneimine.

Further catalysts for the intramolecular elimination of water from alkanolamines in the gas phase are oxide materials which contain silicon or phosphorus as essential components. Catalysts of this type are disclosed, for example, in EP-A-227 461, EP-A-228 898 and EP-A-230 776.

The known catalysts have the disadvantage that undesirable amounts of oligomers and polymers of the aziridine are formed. Furthermore, many of these catalysts have short lives.

It is an object of the present invention to remedy the abovementioned disadvantages.

We have found that this object is achieved by a novel and improved proved process for the preparation of aziridines of the general formula I

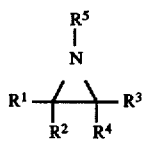

where
$R^1, R^2, R^3$ and $R^4$ are each hydrogen, $C_1$–$C_8$-alkyl, $C_3$–$C_8$-cycloalkyl or aryl and
$R^5$ is hydrogen, $C_1$–$C_8$-alkyl, $C_3$–$C_8$-cycloalkyl, aryl, benzyl, $C_1$–$C_8$-hydroxyalkyl or $C_1$–$C_8$-aminoalkyl,
by converting alkanolamines of the general formula II

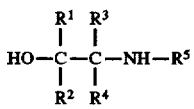

where $R^1$, $R^2$, $R^3$, $R^4$ and $R^5$ have the abovementioned meanings, in the gas phase at from 200° to 600° C. and from 0.001 to 5 bar over heterogeneous catalysts, wherein the heterogeneous catalysts used are presintered moldings.

The novel process can be carried out as follows:

The alkanolamines II can be converted at from 200° to 600° C., preferably from 300° to 550° C., particularly preferably from 350° to 500° C., and from 0.001 to 5, preferably from 0.01 to 2, particularly preferably from 0.1 to 1 bar, in the gas phase over a presintered molding as a heterogeneous catalyst, batchwise or preferably continuously, by a steady-state or circulatory or preferably non-steady-state gas phase procedure, preferably by the fluidized bed procedure.

Examples of suitable presintered moldings are ceramic moldings having uniform pore size in the macropore range or ceramic carrier parts having a uniform pore size in the macropore range and a catalytically active layer adhering firmly thereon.

In the preparation of aziridines I, the dehydration of the alkanolamines II can be carried out in a steady-state or circulating fluidized bed. In the case of the circulating fluidized bed, (non-steady-state procedure), the catalyst is replaced continuously or a little at a time. The catalyst removed from the fluidized-bed reactor can be regenerated in another reactor at from 300° to 800° C., preferably from 400° to 600° C., and from 0.01 to 3, preferably from 0.5 to 1.5, bar, particularly preferably at atmospheric pressure for example in a fluidized bed, in the presence of oxygen, for example in the form of nitrogen and air mixtures. The reaction space in which the dehydration is carried out and the regeneration space in which the finely divided catalyst arriving from the reactor are treated with oxygen must be separate from one another. After the end of the regeneration and the removal of the remaining oxygen, the finely divided catalyst can be recycled to the fluidized-bed reactor. The rate at which the amounts of catalyst are circulated is preferably adapted to the deactivation kinetics of the catalysts. The amounts of catalyst removed from the fluidized-bed reactor are, for example, from 0.1 to 100, preferably from 0.5 to 50, % by weight, of the total amount of catalyst per 24 hours.

The isolation of the resulting aziridines I from the reaction mixture can be carried out, for example, with the aid of an aqueous alkaline absorption liquid and downstream distillation. The aqueous alkaline absorption liquids can be used repeatedly. Suitable liquids of this type are, for example aqueous NaOH or KOH solutions.

Owing to the high reactivity of the aziridines, it is advisable to cool the hot reaction products very rapidly. For example, the hot reaction products emerging from the fluidized-bed reactor can be separated from the gas phase by means of condensed reaction products whose temperature is not more than 40° C. The temperature of the condensed reaction products used for cooling is preferably from −78° to +20° C. Unconverted alkanolamines II can be isolated from the reaction mixture and be used again for the dehydration.

The novel moldings which can be used as catalysts or catalyst carriers possess an extremely monodisperse pore distribution, and, if required, the uniform pore size can be established in the macropore range. The process for the preparation of the moldings is universally applicable to a large number of ceramic powders and powder mixtures. Possible geometries of the moldings are all shapes which can be produced by means of granulation, rolling, compression molding, extrusion or injection molding, for example Raschig rings, wagon wheel profiles, windowframe profiles, honeycomb profiles, saddle elements, star rings, perforated and/or ribbed geometric bodies, such as spheres, right parallelepipeds, cubes, cones, pyramids, prisms, octahedra, cylinders, truncated pyramids and truncated cones, preferably rings, saddle elements, and hollow cones, particularly preferably rings and hollow cones, which as a rule are produced without finishing.

The novel moldings can be prepared by molding a mixture of a ceramic powder and an organic binder, removing the binder by pyrolysis or by treatment with a gaseous acid and sintering to give a residual porosity In general, the moldings can be prepared as follows: After mixing with a thermoplastic material comprising A) from 15 to 70% by volume of a ceramic powder,
B) from 30 to 85% by volume of a polymer which can be molded by a thermoplastic method and
C) from 0 to 15% by volume of a dispersant, for example in a kneader, an extruder or an extruder having shear rolls, these materials can be molded, for example by extrusion or injection molding at from 160° to 250° C., preferably from 170° to 200° C., and from 500 to 2000, preferably from 180 to 190, bar.

The polyacetal-base green compact can be exposed to a gaseous, acid-containing atmosphere. The binder is removed at, as a rule, from 100° to 160° C., preferably from 120° to 140° C., and at from 0.1 to 3 bar, preferably atmospheric pressure, the temperature preferably remaining below the softening temperature of the binder.

The removal of other binder systems can be effected by pyrolysis at from 400° to 800° C. under oxidizing conditions (air), inert gas ($N_2$, Ar, He) or reducing conditions ($N_2/H_2$, Ar/$H_2$).

The strength and final pore distribution of the presintered molding are established as a rule by a presintering process depending on the powder, preferably at from 600° to 1400° C., particularly preferably from 600° to 800° C., under oxidizing conditions (air), inert gas ($N_2$, Ar, He) or reducing conditions ($N_2/H_2$, Ar/$H_2$). The mean pore size depends as a rule mainly on the particle size of the initial powder. As a result of the sintering process, the pore distribution generally becomes narrower while the stability of the porous molding increases.

The presintered moldings, in the form of catalysts or catalyst carriers, generally have a uniform pore size of from 50 nm to 300 µm, and the pore size can be varied by means of the particle size of the powder used.

Examples of suitable ceramic powders are SiC, WC, TiC, TaC, $SiO_2$, $Al_2O_3$, $B_2O_3$, $TiO_2$, $Si_3N_4$, BN, AlN, alkali metal or alkaline earth metal phosphates, arsenates, antimonates, bismuthates, sulfates, selenates, tellurates or mixtures thereof, preferably SiC, WC, TiC, TaC, $SiO_2$, $Al_2O_3$, $B_2O_3$, $TiO_2$ or mixtures thereof, particularly preferably SiC, WC, TiC, TaC or mixtures thereof. The particle size of the powders which may be used is based on nanocrystalline powders from 0.005 to 500 µm, preferably 0.3 to 100 µm, particularly preferably from 0.5 to 50 µm. Furthermore, inorganic fibers or whiskers, comprising, for example, SiC may be added to the materials.

The organic binder may consist of one or more thermoplastic resins, such as polyacetal, polyethylene, polypropylene, polystyrene and polymethylmethacrylate, and one or more plasticizers, such as polyethylene glycol, polypropylene glycol, polybutanediol formal, phthalates and montan ester waxes. These organic binders may be removed by pyrolysis.

In the case of polyacetal binder, polyoxymethylene, which advantageously has a molecular weight of from 10,000 to 500,000, is used. In addition to homopolymers of formaldehyde or trioxane, copolymers of trioxane with, for example, cyclic ethers, such as ethylene oxide and 1,3-dioxolane, or formals, such as 1,3-dioxepan, 1,3-dioxane or mixtures thereof, or homopolymeric poly-1,3-dioxolane, poly-1,3-dioxane or poly-1,3-dioxepan are also suitable, the amounts of the copolymers being in general from 10 to 30% by weight of the polymer.

Assistants, such as dispersants or lubricants, for example polyethylene glycol, or further thermoplastic binders, such as polyethylene, polymethyl methacrylate or polyethylene oxide, may also be present. The amount of assistants is as a rule from 1 to 12% by weight of the total material.

The novel moldings are acidic, neutral and basic catalysts or catalyst carriers, which may be used at temperatures up to, for example, 1000° C. in the case of $Al_2O_3$, 1400° C. in the case of SiC and 800° C. in the case of Fe/Ni.

If required, it is also possible to use carrier materials which have very high mechanical or chemical stability (Fe, SiC, $Si_3N_4$, $Al_2O_3$) and which could not be prepared to date with the novel pore size distribution. Furthermore, highly calcined powders having a substantially inert surface can be compression molded, extruded or injection molded with the novel thermoplastic binder. The abrasion resistance can be increased by increasing the temperature during presintering. Since no active component is present during the calcining of the carrier material, very high strength of the carrier material can be achieved after heating at above 550° C.

The carriers prepared according to the invention have very good water absorption, so that, compared with conventional carriers, more active component can be applied without having to sacrifice the hardness.

The moldings which are used for the preparation of aziridines have, as a rule, a firmly adhering catalytically active layer, preferably in the form of a coat, on the ceramic carriers. Suitable material for the catalytically active layers are all compounds which are known, for example from SU-A-230 166, JP-B-50/10593, WO-A-89/05797, EP-A-227 461, EP-A-228 898 and EP-A-230 776, for the intramolecular elimination of water from alkanolamines II. Preferably used alkali metal, alkaline earth metal or lanthanide compounds or mixtures thereof are those which, under the conditions of the aziridine synthesis, are stable and in particular nonvolatile and form no volatile compounds. Examples of these are phosphates, sulfates, niobates, tungstates, vanadates, manganates, molybdates, rhenates, titanates and salts of heteropoly acids. The catalytically active materials furthermore preferably contain phosphorus, transition metals or mixtures thereof. Examples of such catalytically active materials are lithium-doped tungsten oxide, sodium-doped calcium tungstate and caesium- or barium-doped iron sulfate or nickel sulfate.

Examples of suitable catalytically active materials are those of the general formula III

 (III), where Si is silicon, X is at least one element selected from the group consisting of the alkali metals and alkaline earth metals, Y is an element selected from the group consisting of B, Al, Ti, Zr, Sn, Zn and Ce, and O is oxygen and a, x, y and b are the respective atomic ratios of the elements Si, X, Y and O, and, when a=1, x is from 0.005 to 1, y is from 0 to 1 and b has a value which is determined by a, x and y.

Further suitable catalytically active materials are, for example, those of the general formula IV

 (IV), where X is at least one element selected from alkali metals and alkaline earth metals, P is phosphorus, Y is at least one element selected from B, Al, Si, S, Sc, i, Cu, Y, Zr, Nb, Mo, Sn, Sb, La, Ce, Ta, W, Ti, Pb, Bi and Th, O is oxygen and a, b, c and d are the atomic ratios of the elements X, P, Y and O, and, when a is 1, b is from 0.01 to 3, c is from 0 to 100 and d has a value which is determined by a, b, c and the bonding state of the individual elements.

Further suitable catalytically active materials are, for example, those of the general formula V

 (V), where X is at least one element selected from elements of group IIIA, elements of group IVA, elements of group VA, transition metal elements of groups I to VIII, lanthanide and actinide elements of the Periodic Table, P is phosphorus, X is at least one element selected from alkali metals and alkaline earth metals, O is oxygen and a, b, c and d are the atomic ratios of the elements X, P, Y and O, and, where a is 1, b is from 0.01 to 6, c is from 0 to 3 and d has a value which is determined by a, b and c and the bonding state of the respective elements.

Further suitable catalytically active materials are the oxides of tantalum and niobium, disclosed in U.S. Pat. No. 4,337,175, U.S. Pat. No. 4,289,656, U.S. Pat. No. 4,301,036, U.S. Pat. No. 4,358,405, U.S. Pat. No. 4,376,732 and U.S. Pat. No. 4,477,591, with an alkaline earth metal oxide as promoter.

The catalytically active materials can be applied to the ceramic moldings by physical or chemical methods, for example by impregnation, steeping or physical or chemical vapor deposition under reduced pressure, for example vapor deposition or sputtering.

In the compounds I and II, $R^1, R^2, R^3, R^4$, and $R^5$ are each hydrogen $C_1$–$C_8$-alkyl, such as methyl, ethyl, n-propyl, isopropyl, n-butyl, isobutyl, sec-butyl, tert-butyl, n-pentyl, isopentyl, n-hexyl, isohexyl, n-heptyl, isoheptyl, n-octyl or isooctyl, preferably $C_1$–$C_4$-alkyl, such as methyl, ethyl, n-propyl, isopropyl, n-butyl, isobutyl, sec-butyl or tertbutyl, particularly preferably methyl or ethyl, $C_3$–$C_8$-cycloalkyl, such as cyclopropyl, cyclopentyl, cyclohexyl, cycloheptyl or cyclooctyl, preferably cyclopentyl, cyclohexyl or cyclooctyl, particularly preferably cyclopentyl or cyclohexyl, or aryl such as phenyl, 1-naphthyl or 2-naphthyl, preferably phenyl, and $R^5$ is additionally benzyl, $C_1$–$C_8$-hydroxyalkyl, preferably $C_1$–$C_4$-hydroxyalkyl, such as hydroxymethyl, 1-hydroxyethyl, 2-hydroxyethyl, 1-hydroxy-n-propyl, 2-hydroxy-n-propyl or 3-hydroxy-n-propyl, particularly preferably $C_1$- or $C_2$-hydroxyalkyl, such as hydroxymethyl, 1-hydroxyethyl or 2-hydroxyethyl, or $C_1$–$C_8$-aminoalkyl, preferably $C_1$–$C_4$-aminoalkyl, such as aminomethyl, 1-aminoethyl, 2-aminoethyl, 1-amino-n-propyl, 2-amino-n-propyl or 3-amino-n-propyl, particularly preferably $C_1$–$C_2$-aminoalkyl, such as aminomethyl, 1-aminoethyl or 2-aminoethyl.

EXAMPLES

Preparation of the catalysts A to D
a) Processing of powders to give CIM material The ceramic powders stated in Table 1 were kneaded with a polyoxymethylenecopolymer (POM/PBDF) obtained from trioxane and 2.5% by weight of butanediol formal and having an average molecular weight of 150,000, and with 20% by weight of polybutanediol formal having a molecular weight of 50,000 and 5% by weight (based on the powder used) of polyethylene glycol having a molecular weight of 800 as an assistant, extruded to give extrudates having a diameter of 4 mm and subjected to acid-catalyzed binder removal in a binder-removing oven with 30 ml/h, 100% strength by weight nitric acid at 130° C. under a nitrogen stream of 300 l/h for 10 hours. The heating ($T_1$) shown in Table 1 was then carried out. The pore radius distributions indicated in FIGS. 1 to 3 were obtained with the aid of mercury pressure porosimetry. FIG. 1 refers to catalysts A and C, FIG. 2 to catalyst D, and FIG. 3 to catalyst B.

$b_1$) Application of the active material by spraying 188.6 g of the molding obtained beforehand and freed from binder were processed to give chips (particle size from 2 to 3 mm) and were precalcined at a temperature $T_2$ for 5 hours. The material was introduced into a heated turntable (temperature of the material about 110° C.) and was sprayed with a phosphoric acid solution (6.8 g of 85% strength phosphoric acid in 500 ml of water). The solution was atomized to give a fine dust, which ensured uniform application of the solution to the chips. The duration of spraying was about 4 hours. The sprayed material was subjected to intermediate calcination in an oven at 500° C. for 5 hours and then sprayed in the heated turntable with a solution containing cesium acetate and barium acetate (4.6 g of barium acetate and 6 g of cesium acetate in 500 ml of water). This treatment was carried out similarly to the phosphoric acid treatment. The material was then treated at 500° C. for 5 hours and subjected to free calcination at a temperature $T_3$.

$b_2$) Application of the active material by impregnation 188.6 g of the molding obtained beforehand and freed from binder were processed to give chips (particle size from 2 to 3 mm) and precalcined at a temperature $T_2$ for 5 hours. The material was impregnated with an aqueous phosphoric acid solution (6.8 g of 85% strength phosphoric acid in 500 ml of water) according to its water absorption, dried at 110° C. for 5 hours and subjected to intermediate calcination at 500° C. for 5 hours. The material was then impregnated with a solution containing cesium acetate and barium acetate (4.6 g of barium acetate and 6 g of cesium acetate), according to its water absorption. The impregnated material was dried at 110° C. for 5 hours, calcined at 500° C. for 5 hours and subjected to final calcination at a temperature $T_3$.

TABLE 1

| Catalyst | Carrier material | Heating ($T_1$) [°C.] | Spraying/ impregnation | Precalcination ($T_2$) [°C.] | Final calcination ($T_3$) [°C.] |
|---|---|---|---|---|---|
| A | SiC (Starck, UF15) | 800 | Spraying | 800 | 500 |
| B | ZrO$_2$ (TOSOH, T2-3YS) | 800 | Spraying | 800 | 500 |
| C | SiC (Starck, UF15) | 800 | Impregnation | 800 | 1000 |
| D | Si$_3$N$_4$ (Starck, LC12) | 1000 | Impregnation | 100 | 500 |

Catalyst E
Preparation of calcium phosphate 118.1 g of calcium nitrate tetrahydrate were dissolved in 200 ml of water and heated to 80° C., a solution of 33 g of diammonium phosphate in 100 ml of water was added and the mixture was rendered basic with ammonia and was aged for 30 minutes. After cooling, filtration and washing, the precipitate was dried at 120° C. and calcined for 2 hours at 600° C. The powder obtained was converted into a novel molding according to catalyst preparation a).

Comparative Example I

The powder obtained similarly to catalyst E was kneaded with 5% by weight of methylcellulose and water to give a viscose material and was extruded to give extrudates with a diameter of 3 mm (pressure about 70 bar). The extrudates were dried for 5 hours at 110° C. and calcined for 5 hours at 500° C.

Catalyst F
Preparation of barium phosphate 63.1 g of barium hydroxide octahydrate was suspended in 100 ml of water and heated to 90° C., 18.5 g of diammonium phosphate were added with stirring, the mixture was evaporated down and the residue was dried at 120° C. and calcined at 600° C. for 2 hours. The powder obtained was converted into a novel molding according to catalyst preparation a). The pore radius distribution indicated in FIG. 4 was obtained with the aid of mercury pressure porosimetry.

Comparative Example II

The powder obtained similarly to catalyst F was kneaded with 5% by weight of methylcellulose and water to give a viscose material and was extruded to give extrudates with a diameter of 3 mm (pressure about 70 bar). The extrudates were dried for 5 hours at 110° C. and calcined for 5 hours at 500° C.

Catalyst G

Sodium-containing calcium phosphate 118.1 g of calcium nitrate tetrahydrate were dissolved in 200 ml of water and heated to 80° C., a solution of 107.4 g of disodium hydrogen phosphate dodecahydrate in 200 ml of water was added with stirring, and the mixture was rendered basic with ammonia and aged for 60 minutes. After cooling, filtration and washing, the precipitate was dried at 120° C. and calcined for 2 hours at 500° C. The powder obtained was converted into a novel molding according to catalyst preparation a).

Comparative Example III

The powder obtained similarly to catalyst F was kneaded with 5% by weight of methylcellulose and water to give a viscose material and was extruded to give extrudates in a diameter of 3 mm (pressure about 70 bar). The extrudates were dried for 5 hours at 110° C. and calcined for 5 hours at 500° C.

Preparation of Aziridine 120 l/h of nitrogen and 30 g/h of ethanolamine II (water content of 1% by weight) were metered in a gas-phase procedure into a continuously operated, heatable linear reactor (internal diameter 30 mm, length 300 mm) filled with from 20 to 100 g of catalyst.

The discharges were investigated by gas chromatography, the liquid and gas phases being analyzed separately. The liquid phase was stabilized with sodium hydroxide solution. The results are listed in Tables 2 and 3.

TABLE 2

Reaction temperature 400° C.

| Catalyst | Composition Barium [% by weight] | Cesium [% by weight] | Phosphorus [% by weight] | Conversion [%] | Selectivity [%] | Yield [%] |
|---|---|---|---|---|---|---|
| A | 1.3 | 2.1 | 1 | 81.2 | 9.1 | 7.4 |
| B | 1.3 | 2.1 | 1 | 68.4 | 6.8 | 4.7 |
| C | 1.35 | 2.3 | 0.9 | 57.7 | 56.3 | 32.5 |
| D | 1.3 | 2.1 | 1 | 84.7 | 13.8 | 11.7 |
| E | | | | 88.6 | 4.3 | 3.8 |
| F | 68.4 | 0 | 10.3 | 81.4 | 41.3 | 33.6 |
| G | | | | 95.6 | 11 | 10.5 |
| V-I | | | | 33.7 | 0 | 0 |
| V-II | 67 | 0 | 12.2 | 27.9 | 10.1 | 2.8 |
| V-III | | | | 45.4 | 4 | 1.8 |

TABLE 3

Reaction temperature 450° C.

| Catalyst | Composition Barium [% by weight] | Cesium [% by weight] | Phosphorus [% by weight] | Conversion [%] | Selectivity [%] | Yield [%] |
|---|---|---|---|---|---|---|
| A | 1.3 | 2.1 | 1 | 69.1 | 7.3 | 5 |
| B | 1.3 | 2.1 | 1 | 35.5 | 3.8 | 1.3 |
| C | 1.35 | 2.3 | 0.9 | 51.7 | 44.4 | 23 |
| D | 1.3 | 2.1 | 1 | 52.2 | 5.9 | 3.1 |
| E | | | | 62.6 | 1.6 | 1 |
| F | 68.4 | 0 | 10.3 | 62.1 | 67.1 | 41.7 |
| G | | | | 78.6 | 54.8 | 43.1 |
| V-I | | | | 17.4 | 0 | 0 |
| V-II | 67 | 0 | 12.2 | 30.6 | 15.3 | 4.7 |
| V-III | | | | 32.9 | 2.2 | 0.7 |

We claim:

1. A process for the preparation of aziridines of the formula I

where
R¹, R², R³ and R⁴ are each hydrogen, $C_1$–$C_8$-alkyl, $C_3$–$C_8$-cycloalkyl or aryl and
R⁵ is hydrogen, $C_1$–$C_8$-alkyl, $C_3$–$C_8$-cycloalkyl, aryl, benzyl, $C_1$–$C_8$-hydroxyalkyl or $C_1C_8$-aminoalkyl,
by converting alkanolamines of the formula II

where R¹, R², R³, R⁴ and R⁵ have the abovementioned meanings, in the gas phase at from 200° to 600° C. and from 0.001 to 5 bar over heterogeneous catalysts, wherein the heterogeneous catalysts used are presintered moldings maintained as a fluidized bed.

2. A process for the preparation of aziridines as claimed in claim 1, wherein the reaction is carried out in said fluidized bed at from 0.001 to 2 bar.

3. A process for the preparation of aziridines as claimed in claim 1, wherein the reaction is carried out at from 0.01 to 1 bar.

4. A process for the preparation of aziridines as claimed in claim 1, wherein the reaction is carried out in a steady-state fluidized bed.

5. A process for the preparation of aziridines as claimed in claim 1, wherein presintered fluidizable moldings having a uniform pore size of from 50 nm to 300 μm are used, said moldings being prepared by steps including a) molding a mixture of a ceramic powder and an organic binder to give a thermoplastic material by granulation, compression molding, rolling, extrusion or injection molding, b) removing the binder by pyrolysis or by treatment with gaseous acid and c) sintering.

6. A process for the preparation of aziridines as claimed in claim 1, wherein, prior to sintering, the moldings are thermoplastic materials comprising A) from 15 to 70% by volume of a ceramic powder, B) from 30 to 85% by volume of a polymer which is molded by a thermoplastic method and C) from 0 to 15% by volume of a dispersant.

7. A process for the preparation of aziridines as claimed in claim 6, wherein the ceramic powders A) in the moldings are oxidic, carbidic or nitridic powders, including $SiO_2$, $Al_2O_3$, $TiO_2$, $ZrO_2$, $B_2O_3$, $Y_2O_3$, $Si_3N_4$, BN, AlN, TiN, ZrN, SiC, TiC, WC, $B_4C$ or mixtures thereof.

8. A process for the preparation of aziridines as claimed in claim 6, wherein the ceramic powders A) in the molding are alkali metal or alkaline earth metal phosphates, arsenates, antiomates, bismuthates, selenates, tellurates or mixtures thereof.

9. A process for the preparation of aziridines as claimed in claim 6, wherein the ceramic powders A) in the moldings are tungstates, niobates, tungstosilicic acids or mixtures thereof.

10. A process for the preparation of aziridines as claimed in claim 6, wherein the moldings carry a firmly adhering catalytically active layer of an element of the alkali metal, alkaline earth metal or lanthanide series or mixtures thereof.

11. A process for the preparation of aziridines as claimed in claim 6, wherein the moldings have a firmly adhering catalytically active layer of compounds of main group elements of the 3 to 7.

12. A process as claimed in claim 1, wherein the reaction is carried out in a circulating fluidized bed of said presintered molding of the heterogeneous catalyst.

13. A process as claimed in claim 12, wherein the hot reaction products emerging from the circulating fluidized bed reactor are separated from the gas phase by rapid cooling at a condensation temperature of not more than 40° C.

14. A process as claimed in claim 12, wherein any unreacted alkanolamine (II) is isolated from the reaction products and returned to the gas phase reaction.

15. A process as claimed in claim 12, wherein the fluidized catalyst removed from the reaction zone of the fluidized bed reactor is regenerated in another separate fluidized bed reactor at from 300° to 800° C. and from 0.01 to 3 bar in the presence of oxygen and recycled to the gas phase reaction of the alkanolamine reactant (II).

* * * * *

UNITED STATES PATENT AND TRADEMARK OFFICE
CERTIFICATE OF CORRECTION

PATENT NO. : 5,693,825
DATED : Dec. 2, 1997
INVENTOR(S) : Dingerdissen et al

It is certified that error appears in the above-indentified patent and that said Letters Patent is hereby corrected as shown below:

In Claim 11, line 3: cancel "main group" and substitute --the--.

In Claim 11, last line: cancel "the" and substitute --main groups--.

Signed and Sealed this

Thirty-first Day of March, 1998

Attest:

BRUCE LEHMAN

Attesting Officer

Commissioner of Patents and Trademarks